(12) United States Patent
Shin et al.

US009751941B2

(10) Patent No.: US 9,751,941 B2
(45) Date of Patent: Sep. 5, 2017

(54) ANTIGEN DERIVED FROM EXTRACELLULAR DOMAIN OF MULTI-TRANSMEMBRANE PROTEIN AND USES THEREOF

(71) Applicant: REFERENCE BIOLABS Inc., Seoul (KR)

(72) Inventors: Young Kee Shin, Seoul (KR); Young-Deug Kim, Incheon (KR); Jun Young Choi, Gwangmyeong-si (KR); Myung Seok Lee, Seoul (KR)

(73) Assignee: Abion Inc., Seoul (KR)

( * ) Notice: Subject to any disclaimer, the term of this patent is extended or adjusted under 35 U.S.C. 154(b) by 948 days.

(21) Appl. No.: 13/803,090

(22) Filed: Mar. 14, 2013

(65) Prior Publication Data

US 2014/0274755 A1  Sep. 18, 2014

(51) Int. Cl.
*C07K 5/00* (2006.01)
*C07K 5/12* (2006.01)
*C07K 7/04* (2006.01)
*C07K 14/00* (2006.01)
*C07K 16/28* (2006.01)

(52) U.S. Cl.
CPC .......... *C07K 16/28* (2013.01); *C07K 2317/24* (2013.01); *C07K 2317/34* (2013.01); *C07K 2317/622* (2013.01)

(58) Field of Classification Search
None
See application file for complete search history.

(56) References Cited

FOREIGN PATENT DOCUMENTS

KR    20120091997 A  *  8/2012

OTHER PUBLICATIONS

Kolchanov, 1988, Journal of Molecular Evolution, vol. 27, pp. 154-162.*
Pasquo, 2012, PLoS One, vol. 7, Issue 2, e32555.*
Bork, 2000, Genome Research 10:398-400.*
Bork et al., 1996, Trends in Genetics 12:425-427.*
KR2012091997-A (Pub Date Aug. 20, 2012) Machine translation, p. 1-23.*
Alexander R. Kazarov, et al., An extracellular site on tetraspanin CD151 determines alpha3 and alpha6 integrin-dependent cellular morphology, The Journal of Cell Biology, vol. 158, No. 7, Sep. 30, 2002, 1299-1309.
George A. Cook et al., Identification of CD9 extracellular domains important in regulation of CHO cell adhesion to fibronectin and fibronectin pericellular matrix assembly, Blood, 100: 4502-4511 (2002).
Andrea E. Varga et al. Methylation of a CpG Island within the Uroplakin Ib Promoter: A Possible Mechanism for Loss of Uroplakin Ib Expression in Bladder Carcinoma, Neoplasia . vol. 6, No. 2, Mar./Apr. 2004, pp. 128-135.

* cited by examiner

*Primary Examiner* — Christine J Saoud
*Assistant Examiner* — Jegatheesan Seharaseyon
(74) *Attorney, Agent, or Firm* — Clark & Elbing LLP; Susan M. Michaud

(57) ABSTRACT

A multi-transmembrane protein antigen includes a polypeptide corresponding to an extracellular loop of the multi-transmembrane protein, the N-terminal and C-terminal of the polypeptide being fixed on a solid substrate or the N-terminal and C-terminal being attached to both ends of a linker to form a cyclic structure, an antibody specifically binding to the antigen or an antigen-binding fragment thereof, and a method for screening an antibody specifically binding to the antigen. The present invention may be usefully employed for effective production of antibodies for multi-transmembrane proteins that play important roles in disease-related phenomena such as cell signaling.

6 Claims, 11 Drawing Sheets

| Rank | Time | Name | Conc. | Area | Height |
|---|---|---|---|---|---|
| 1 | 11.431 | | 0.2207 | 21750 | 2988 |
| 2 | 11.602 | | 0.3236 | 31891 | 5194 |
| 3 | 12.881 | | 0.6521 | 64264 | 4815 |
| 4 | 14.141 | | 96.95 | 9554321 | 459483 |
| 5 | 14.475 | | 1.861 | 183391 | 46053 |
| Total | | | 100 | 9855617 | 518533 |

FIG. 8
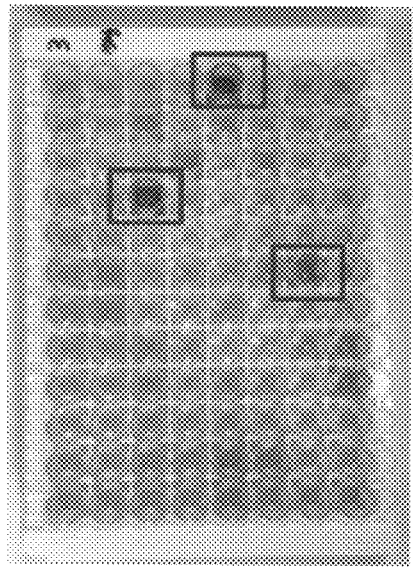
CLDN3 – BSA conjugated cyclic form
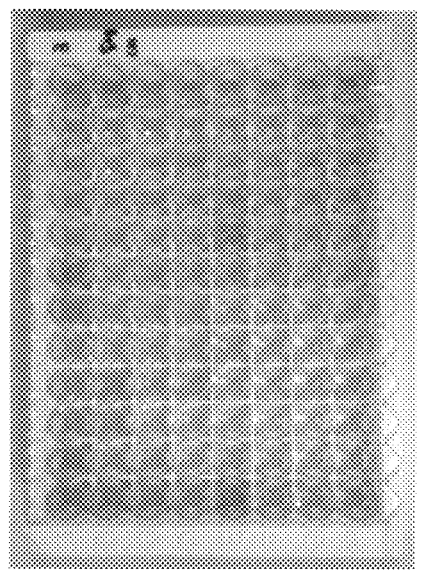
CLDN3 – BSA conjugated linear form

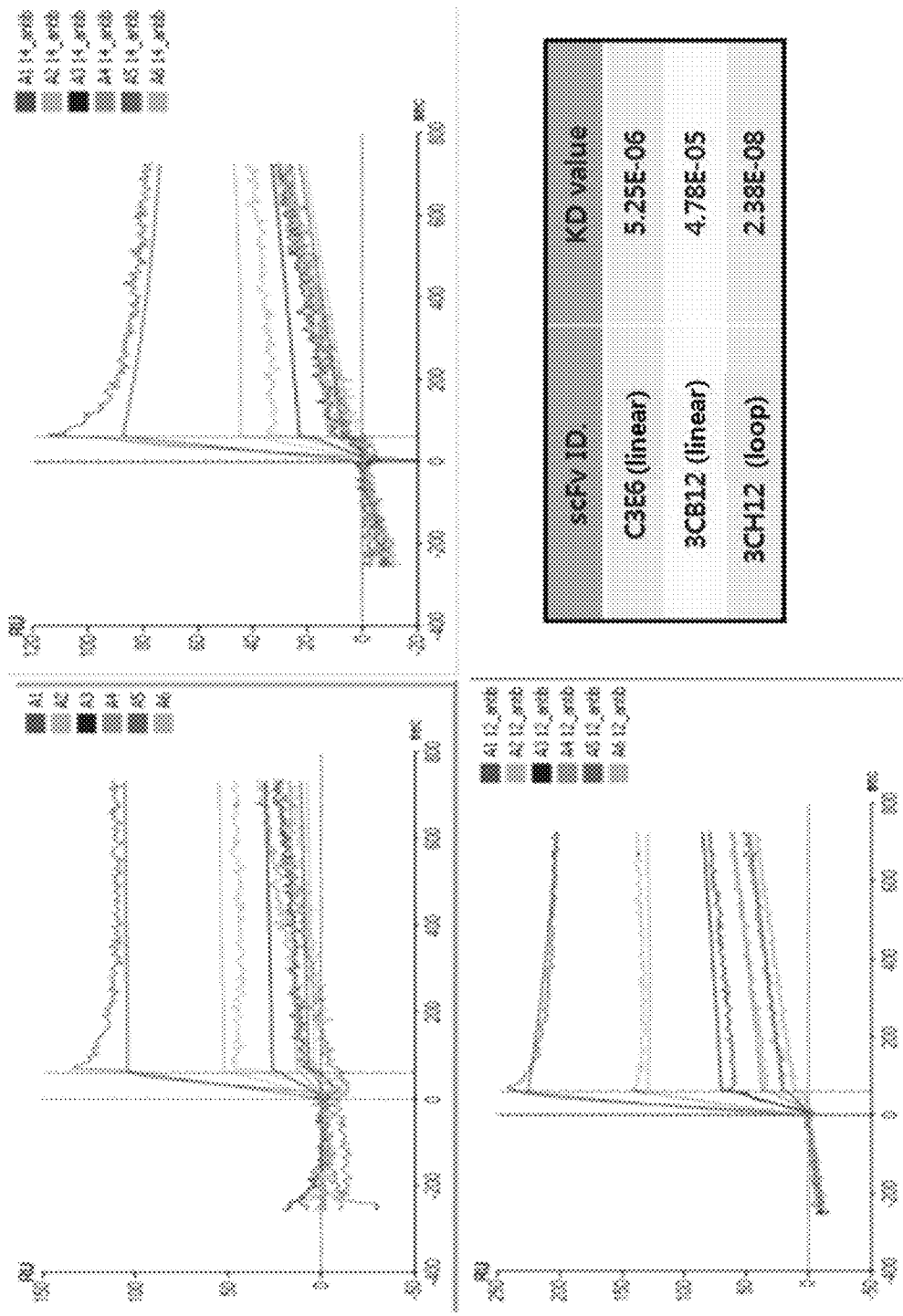

ANTIGEN DERIVED FROM EXTRACELLULAR DOMAIN OF MULTI-TRANSMEMBRANE PROTEIN AND USES THEREOF

BACKGROUND

1. Field of the Invention

The present invention relates to an antigen including a polypeptide of an extracellular loop of the multi-transmembrane protein, and a method for screening and preparing the antibodies therewith.

2. Description of the Related Art

Since transmembrane proteins exist in human genome in large numbers (more than 7,000 kinds) and are importantly involved in disease-related phenomena such as cell signaling, they have been major target antigens for antibody therapy. As proteins that pass through the cell membrane 1 or 2 times, there are receptor proteins (about 400 kinds), enzyme proteins (about 500 kinds) and other cell membrane proteins (about 500 kinds). Also, there are various multi-transmembrane proteins that pass through the cell membrane 3 or more times, including receptor proteins (about 1000 kinds), most transport proteins (about 800 kinds) and proteins necessary for tight junction between cells. In order to develop useful antibodies using various transmembrane proteins, it is essential to secure antigens of high quality that maintain the natural state. In particular, for protein antigens, it is known that high-quality antibodies can be prepared when not only purity of protein but also 3-dimensional structure and physiological activity thereof are ensured. Although many researchers have prepared antigens using various transmembrane proteins, it was difficult to obtain superior antibodies for transmembrane proteins since they are mostly linear. Since antibodies are prepared mostly for the N-terminal or C-terminal region exposed to the cytoplasm or out of the cell membrane, they do not exert sufficient effect desired for the antibodies. Although transmembrane proteins are a very good target for research of diseases since they play important roles between cells or tissues, proteins prepared, for example, by recombination often have two or more transmembrane domains and do not maintain the natural state of being bound to the membrane in vivo. Further, coexistence of lipid components makes it difficult to obtain high-quality antibody. Many researchers have merely used expression products of transmembrane proteins obtained through a biological process or those obtained through selective synthesis of specific regions as antigens. Other researchers are studying fusion of transmembrane proteins with Fc of human antibodies for expression using animal cells in order to prepare antigens of various transmembrane proteins. However, the probability of the expressed proteins being expressed well in the animal cells and being presented as transmembrane proteins is low and a lot of time and cost are required for the development. Since multi-transmembrane proteins having two or more transmembrane domains naturally have an extracellular loop, the inventors of the present disclosure have devised a method of mimicking the regions and preparing a single-loop peptide using, for example, a linker for use as an antigen.

An antibody is a protein produced by the immune system. With high specificity for antigens as compared to small molecules, antibodies inactivate or remove antigens and thus can be a very efficient drug with few side effects. For example, transmembrane proteins exhibiting specific expression profile on the surface of cancer cells may be used as a target for antibody therapy for killing the cancer cells using immune cells or Immunomodulators. Also, the antibody may be used to selectively treat only the cancer cells as a carrier of radioisotopes or toxins (antibody-directed enzyme prodrug therapy; ADEPT). Although human antibodies are ideal for the antibody therapy, development thereof has been retarded due to the inability of production thereof by the hybridoma technology using human cells. Recently, the phage display technique that enables the production of human monoclonal antibodies without resorting to the human hybridoma technology is gaining a lot of attentions.

Researches are being focused on the claudin family with regard to the relationship between transmembrane proteins and cancer. Claudins are a family of cell membrane proteins with a molecular weight of approximately 20-34 kDa which have four transmembrane domains and constitute tight junctions. The claudin family includes 23-24 members in human and mice and each member of the claudins is known to exhibit a very unique expression pattern depending on each epithelial cell type (Furuse and Tsukita, *Trends in Cell Biology* 16: 181 (2006); Wilcox, et al., *Cell* 104: 165 (2001); Rahner, et al., *Gastroenterology* 120: 411 (2001)). In the sheet of epithelial cells, a mechanism works to prevent substances from leaking (diffusing) in the intercellular spaces and cell-cell adhesion systems called the tight junctions have been shown to actually play a critical role as a "barrier" in the mechanism to prevent leakage. A general structure of the claudin protein is described in detail in FIG. 1 (Lai-Nag M et. al *Genomic Biology* 2009, 10: 235 (2009)). It is reported that the expression of the claudin protein is closely related with cancer. In particular, it is known that claudin-1 suppresses breast cancer and prostate cancer and decreased expression of claudin-7 in esophageal carcinoma leads to increase of cancer cells owing to loss of E-cadherin. Since increased or decreased expression of the highly specific claudin protein in human cancer tissues is indicative of carcinogenesis, it may be a useful biomarker for detection, diagnosis and treatment of cancer. In particular, the expression of CLDN 3 and 4 is increased in various cancers and it is actively studied as a biomarker for ovarian cancer for which no useful drug has been developed yet (Choi et al., *Histol Histopathol* 22: 1185-1195 (2007)). Most antibodies developed using CLDN 3 and 4 are based on linear imaginary peptides as antigens.

CD151, also known as PETA-3 or SFA-1, is a protein in the tetraspanin family (Boucheix and Rubinstein, *Cell Mol. Life Sci.* 58: 1189-1205 (2001); Korean Patent Application Publication No. 2011-0010708; Hemler M E, *J. Cell Biol.* 155: 1103-1107 (2001)). In human, CD151 has 253 amino acids and includes four membrane fragments and two extracellular domains EC1 (18 amino acids, sequences 40-57) and EC2 (109 amino acids, sequences 113-221) which are called extracellular loops. In the nucleotide sequence of CD151, two variants of CD151 have been identified hitherto, i.e. one having nucleotides A and C at positions 395 and 409, respectively (Fitter et al., *Blood* 86 (4):1348-1355 (1995)) and the other having nucleotides G and T instead of the nucleotides A and C (Hasegawa et al., *J. Virol.* 70 (5): 3258-3263 (1996)). They have been identified as mutation of the residues K (Lys) and P (Pro) to the residues R (Arg) and S (Ser) at the positions 132 and 137 in the peptide sequence, respectively. CD151 interacts on the cell surface with various membrane proteins. Specifically, highly stable complexes resistant to the action of certain detergents with laminin receptor integrins, more specifically with integrin α3β1 or α6β4, whose preferred ligand is laminin 5, have been identified (Yauch et al., *Mol. Biol. Cell* 9:2751-2765 (1998); Lammerding et al., *Proc. Natl. Acad. Sci. USA* 100:7616-7621 (2003)). The association of these complexes involves the extracellular domains of CD151 and integrin. The QRD sequence [194-196] of CD151, located in the ECL2 loop, is very important in that association because mutation of this site causes loss of interaction with certain integrins (Kazarov et al., *J. Cell Biol.* 158: 1299-1309 (2002)).

Some previous researches have shown that overexpression of CD151 is associated with aggressiveness of certain cancers, such as lung, colon and prostate cancer, and that it might be considered to be a factor for poor prognosis (Tokuhara et al., *Clin. Cancer Res.* 7: 4109-4114 (2001); Hashida et al., *Br. J. Cancer* 89: 158-167 (2003); Ang et al., *Cancer Epidemiol. Biomarkers Prev.* 13: 1717-1721 (2004)). In these cases, mean survival rate was in fact decreased in those patients having tumors which express CD151, compared to those having tumors which do not express CD151. The overexpression of CD151 in various human tumor lines (HeLa, RPMI4788, A172, HT1080), brought about by transfection of the corresponding gene, causes increase in motility, migration and invasion of the transfected cells. Since these phenomena are inhibited in the presence of anti-CD151 antibodies (Testa et al., *Cancer Res.* 59: 3812-3820 (1999); Kohno et al., *Int. J. Cancer* 97: 336-343 (2002)), they can be a very important target in the development of anti-cancer drugs.

CD9 is also a cell surface glycoprotein receptor belonging to the tetraspanin family with a molecular weight of about 24-27 kD and is known to regulate signal transduction events playing important roles in development, activity and motility of cells. In addition, CD9 is known to be capable of regulating cell adhesion (Anton, E. S., et al., *J. Neurosci.* 15: 584-595, 1995) and cell migration (Klein-Soyer, C., et al., *Arterioscler Thromb Vasc Biol.* 20: 360-369, 2000) and triggering platelet activation and aggregation which are involved in platelet-induced endothelial cell proliferation (Masellis Smith, A., and Shaw, A. R., *J. Immunol.* 152: 2768-2777 (1994)). Moreover, it is known to be involved in various cellular phenomena such as promotion of muscle cell fusion and myotube maintenance. It is reported that the second extracellular loop (extracellular loop 2; ECL2) of CD9 is important in cell adhesion (George, A., et al., *Blood* 100: 4502-4511, 2002) and in promoting activity of DTR toward diphtheria toxin (DT) (Hidetoshi, H., et al. 289: 782-790 (2001)). In addition, although the ECL2 domain is glycosylated in many other tetraspanin family proteins, CD9 is distinguished in that the ECL1 domain is glycosylated. CD9 is reported to be related with cell motility and tumor metastasis (Miyake, M. and Hakomori, S., *Biochemistry* 30: 3328-3334, (1991)). It is presumed that CD9 exhibits tissue-specific aspects in cancer. Decreased expression of CD9 was observed in colon cancer (Mori, M., et al., *Clin. Cancer Res.* 4: 1507-1510 (1998)), breast cancer (Miyake, M., et al., *Cancer Res.* 55: 4127-4131 (1995)), lung cancer (Higachiyama, M., et al., *Cancer Res.* 55: 6040-6044 (1995); Funakoshi, T., et al., *Oncogene* 22: 674-687 (2003)) and pancreatic cancer (Sho, M., et al., *Int. J. Cancer* 79: 509-516 (1998)) patients and it is reported that it is associated with invasion, metastasis and poor prognosis of patients. However, there are some reports that the expression of CD9 is increased in head and neck squamous cell carcinoma (Erovic, B. M., et al., *Head Neck* 25: 848-857 (2003)) and stomach cancer (Hori, H., et al., *J. Surg. Res.* 117: 208-215 (2004)) with the progression of cancer.

Uroplakin 1B (UPK1B) is another member of the human tetraspanin family. It is a cell surface protein characterized by the presence of four hydrophobic domains. The protein mediates signal transduction events that play a role in the regulation of cell development, activation, growth and motility. In particular, interaction between the asymmetrical unit membrane (AUM) and the cytoskeleton is related with cancer and the relationship between the methylation of a CpG island with the UPK1B promoter and bladder cancer is well known (Varga A E, Leonardos L, Jackson P, Marreiros A, Cowled P A., *Neoplasia*. March-April; 6 (2): 128-35 (2004)).

Recently, the above-described membrane proteins are reported to be related with cancers. Although antibodies are being developed using specific regions thereof, they are mostly prepared based on linear imaginary peptides or partially expressed proteins as antigens.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY

The present inventor has made intensive studies to develop a method for effectively producing antibodies for multi-transmembrane proteins that play important roles in disease-related phenomena such as cell signaling. As results, the present inventors have discovered that a superior antibody with remarkable efficiency may be obtained when a single-loop peptide, which mimics the loop providing connection between transmembrane domains, is used as an antigen Accordingly, it is an aspect of this invention to provide a multi-transmembrane protein antigen.

It is another aspect of this invention to provide an antibody specifically binding to the multi-transmembrane protein or an antigen-binding fragment thereof.

It is still another aspect of this invention to provide a method for screening an antibody specifically binding to the multi-transmembrane protein antigen.

Other aspects and advantages of the present invention will become apparent from the following detailed description together with the appended claims and drawings.

BRIEF DESCRIPTION OF THE DRAWINGS

FIG. 8 shows a result of analyzing the efficiency of selected loop-type and linear antibodies by ELISA.

FIG. 10 shows a result of analyzing the efficiency of selected loop-type and linear antibodies by SPR. Binding abilities of C3E6 (top left) and C3B12 (top right), which are antibody fragments derived from a linear antigen, and 3CH12 (bottom), which is an antibody fragment derived from a loop-type antigen, were evaluated by measuring dissociation constants (KD) at various concentrations.

DETAILED DESCRIPTION

Figure 1:
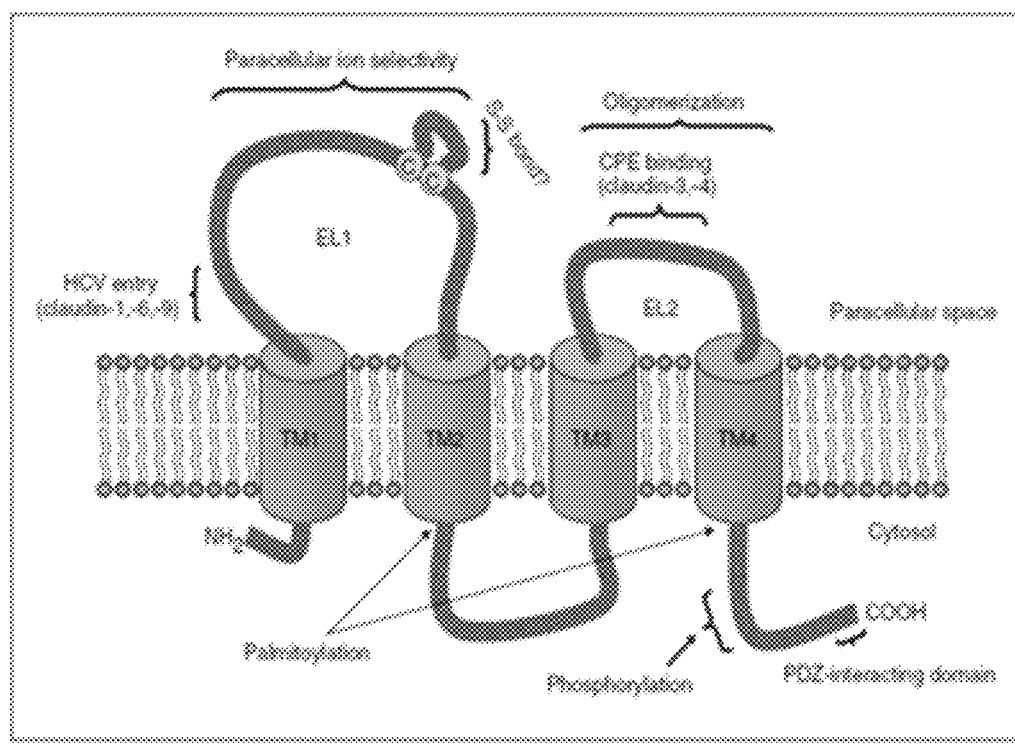
FIG. 1 schematically shows a multi-transmembrane protein.

In one aspect of this invention, there is provided a multi-transmembrane protein antigen including a polypeptide of an extracellular loop of the multi-transmembrane protein, wherein an N-terminal and a C-terminal of the polypeptide are fixed on a solid substrate.

The present inventor has made intensive studies to develop a method for effectively producing antibodies for multi-transmembrane proteins that play important roles in disease-related phenomena such as cell signaling. As results, the present inventors have discovered that a superior antibody with remarkable efficiency may be obtained when a single-loop peptide, which mimics the loop providing connection between transmembrane domains, is used as an antigen.

The term "polypeptide" as used herein, refers to a linear molecule formed from amino acid residues linked by peptide bonding. The polypeptide of the present disclosure may be prepared by a molecular biological method and a chemical synthesis method known in the art, in particular, the solid-phase synthesis technique (Merrifield, *J. Amer. Chem. Soc.* 85: 2149-54 (1963); Stewart, et al., Solid Phase Peptide Synthesis, 2nd. ed., Pierce Chem. Co.: Rockford, 111 (1984), which is incorporated herein by reference).

The term "multi-transmembrane protein" as used herein, refers to a membrane protein having two or more transmembrane domains and an extracellular loop connecting them.

In accordance with the present disclosure, an antigen prepared by mimicking a polypeptide having an extracellular loop has a much higher affinity for and binding ability to an antibody as compared to a linear imaginary peptide obtained by expressing a transmembrane protein as it is. In accordance with the present disclosure, efficiency and specificity as an antigen are greatly improved by fixing both ends of the polypeptide of the extracellular loop on a solid substrate and thereby completely mimicking the stereostructure of the transmembrane region in the multi-transmembrane protein which is attached to a membrane in vivo.

The solid substrate used in the present disclosure may be any to which a polypeptide chain can be attached via covalent or non-covalent bonding with a peptide residue and may be any one commonly used in the related art without limitation.

Owing to the high efficiency and specificity, the antigen of the present disclosure may be used for regulation of the receptor protein of a membrane protein, regulation of the transport pathway protein of a membrane protein and regulation of the protein involved in tight junction between cells, and thus may be effectively used for studying cell signaling.

According to an embodiment, the polypeptide of the extracellular loop of the multi-transmembrane protein is a polypeptide having an amino acid sequence selected from the group consisting of SEQ ID NOS: 1 through 21.

In accordance with embodiments of the present disclosure, the amino acid sequences of SEQ ID NOs: 1 through 21 are extracellular loop amino acid sequences of CD-151-1 through CD-151-6, which are multi-transmembrane proteins; claudin 3 to 7, 9 and 17; CPE; CD9-1 to 3 or UP1b-1 to 3, which are multi-transmembrane proteins.

More specifically, the polypeptide of the extracellular loop of the multi-transmembrane protein is a polypeptide having an amino acid sequence of SEQ ID NO: 3 or 4.

The amino acid sequences of SEQ ID NO: 3 and SEQ ID NO: 4 are respectively the amino acid sequences of the polypeptide of the extracellular loop of claudin 3 (CLDN 3) and claudin 4 (CLDN 4). Accordingly, the antibodies produced from these antigens may be used for diagnosis of various cancers where the expression of CLDN 3 or CLDN 4 is increased or for screening of therapeutic agents.

In another aspect of this invention, there is provided a multi-transmembrane protein antigen including a polypeptide of an extracellular loop of the multi-transmembrane protein, wherein an N-terminal and a C-terminal of the polypeptide are attached to both ends of a linker to form a cyclic structure.

As the common descriptions regarding the polypeptide of the extracellular loop of the multi-transmembrane protein of this invention are mentioned above, they are omitted herein to avoid excessive overlaps.

The term "linker" as used herein, refers to a molecule which connects the N-terminal and the C-terminal of the polypeptide of the present disclosure via covalent or non-covalent bonding. The linker of the present disclosure may reproduce a 3-dimensional structure similar to the natural structure of a loop providing connection with a neighboring transmembrane region by making the molecule have a cyclic structure. The length of the linker of the present disclosure may be selected such that the polypeptide has an optimized stereostructure. Specifically, the linker of the present disclosure is selected from a group consisting of aminohexanoic acid, polyglycine and polyalanine.

According to an embodiment, the linker of this invention is attached to a water-soluble resin.

In accordance with the present disclosure, the antigen of the present disclosure may be attached to the water-soluble resin as a support for easier and more efficient use for antibody screening. In particular, when the antibody is obtained by solid-phase synthesis, the linker of the present disclosure may be fixed onto the resin. The resin used in the present disclosure may be any natural or synthetic resin employed in the art. Specifically, a chlorotrityl chloride (CTL) resin may be used. Specifically, the resin of the present disclosure may be enclosed by polyethylene glycol (PEG) to provide water solubility.

In still another aspect of this invention, there is provided an antibody specifically binding to the multi-transmembrane protein antigen including a polypeptide of an extracellular loop of the multi-transmembrane protein, wherein an N-terminal and a C-terminal of the polypeptide are fixed on a solid substrate or an antigen-binding fragment thereof. The antibody of the present disclosure may be a polyclonal or monoclonal antibody, specifically a monoclonal antibody.

The term "antigen-binding fragment of an antibody" (or "antibody fragment") as used herein, refers to one or more fragment of an antibody that retains the ability to bind specifically to the antigen of the present disclosure. For example, the antibody fragment may include, not limited to, Fab fragment, F(ab')2 fragment, scFv fragment, dAb fragment, CDR-containing fragment or isolated CDR. The Fab and F(ab')2 fragments lack the Fc fragment as compared to the complete antibody. Accordingly, they may be cleared from circulation in an animal or plant more quickly and may exhibit less non-specific tissue binding as compared to the complete antibody.

The antibody for the antigen of the present disclosure or the antigen-binding fragment thereof may be prepared according to methods commonly employed in the art, for example, fusion (Kohler and Milstein, *European Journal of Immunology*, 6: 511-519 (1976)), recombinant DNA method (U.S. Pat. No. 4,816,567) or phage antibody library method (Clackson et al, *Nature*, 352: 624-628 (1991); Marks et al, *J. Mol. Biol.*, 222: 58, 1-597 (1991)), which are incorporated herein by reference. General procedures for preparing the antibody are described in detail in Harlow, E. and Lane, D., Using Antibodies: A Laboratory Manual, Cold Spring Harbor Press, New York, 1999, Zola, H., Monoclonal Antibodies: A Manual of Techniques, CRC Press, Inc., Boca Raton, Fla., 1984, and Coligan, Current Protocols in Immunology, Wiley/Greene, N.Y., 1991, which are incorporated herein by reference. For example, hybridoma cells producing monoclonal antibodies may be prepared by fusing immortalized cells with antibody-producing lymphocytes, which is well known to and can be easily carried out by those skilled in the art. Polyclonal antibodies can be obtained by injecting the antigen of the present disclosure to an appropriate animal, collecting an antiserum from the animal and isolating antibodies from the antiserum according to a known affinity-based technique. The antigen-binding fragment of the antibody can be screened in the same manner as the complete antibody.

The term "specifically binding" as used herein, means that an antibody or an antigen-binding fragment thereof forms a complex with an antigen under stable physiological conditions. The specific binding can be characterized by an equilibrium dissociation constant not greater than about $1 \times 10^{-6}$ M. Methods for determining whether two molecules specifically bind to each other are well known in the art and include, for example, equilibrium dialysis, surface plasmon resonance, and the like.

The antibody of the present disclosure or an antigen-binding fragment thereof may be conjugated with a bioactive agent. The term "bioactive agent" as used herein, refers to any synthetic or naturally occurring compound that binds to an antigen and enhances a desired activity by mediating a desired biological effect. For example, the antibody of the present disclosure or a fragment thereof may be conjugated with a cytotoxin, a chemotherapeutic drug, an immunosuppressor or a radioisotope.

In still another aspect of this invention, there is provided a method for screening an antibody specifically binding to the multi-transmembrane protein antigen, including contacting the multi-transmembrane protein with a humanized antibody library.

As the common descriptions regarding the antigen and the antibody specifically binding thereto used in this invention are mentioned above, they are omitted herein to avoid excessive overlaps.

Methods for screening an antibody specifically binding to a particular antigen are well known in the art. For example, the phage library display method (Clackson et al, *Nature*, 352: 624-628 (1991); Marks et al, *J. Mol. Biol.*, 222: 58, 1-597 (1991), which is incorporated herein by reference) may be used. As an example, the antigen of the present disclosure peptide bound to a bead is reacted with a solution of humanized antibody library. Then, the bead is recovered and separated from the humanized antibody library using a membrane filter tube. The separated solution of humanized antibody library is inoculated to cells and, after culturing, the cells are infected with a helper phage. The culture is centrifuged and the supernatant is recovered. This procedure is repeated. By measuring the titer of the library candidates panned from the cells, antibodies with high reactivity may be screened.

The features and advantages of one or more embodiments of the present invention will be summarized as follows:

(a) One or more embodiments of the present invention provides a multi-transmembrane protein antigen including a polypeptide of an extracellular loop of the multi-transmembrane protein, the N-terminal and C-terminal of the polypeptide being fixed on a solid substrate or the N-terminal and C-terminal being attached to both ends of a linker to form a cyclic structure, an antibody specifically binding to the antigen or an antigen-binding fragment thereof, and a method for screening an antibody specifically binding to the antigen.

(b) One or more embodiments of the present invention may be usefully employed for effective production of antibodies for multi-transmembrane proteins that play important roles in disease-related phenomena such as cell signaling.

(c) One or more embodiments of the loop-type antigen of the present invention exhibits much stronger affinity as compared to the existing linear antigens by completely mimicking the loop stereostructure of multi-transmembrane proteins in vivo.

(d) One or more embodiments of the present invention may be employed for effective screening of antibodies and may be used for, depending on the properties of the particular transmembrane protein, prevention and treatment of cancer and inflammation, and for diagnosis of high reliability.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Synthesis of Loop-Type Peptide

Figure 2:
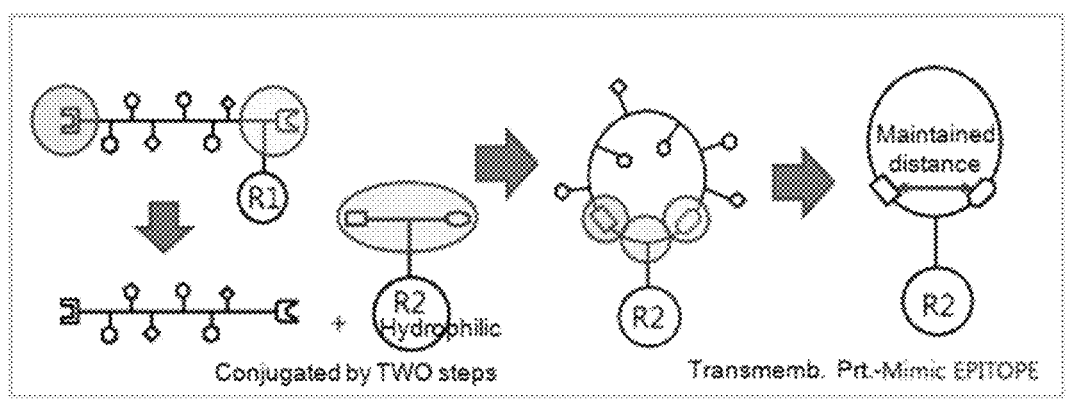
FIG. 2 schematically describes synthesis of a loop-type peptide.

In order to prepare a loop-type peptide antigen of SEQ ID NO: 1, synthesis was carried out in two stages, as follows. The synthesis was conducted as schematically described in FIG. 2.

(1) Synthesis of Protecting Group-Attached Peptide 700 mg of a chlorotrityl chloride (CTL) resin (Nova Biochem, Cat No. 01-64-0021) was added to a reactor and stirred for 3 minutes after adding 10 mL of methylene chloride (MC). After removing the solution and adding 10 mL of dimethylformamide (DMF), the mixture was stirred for 3 minutes and then the solvent was removed. After adding 10 mL of dichloromethane to the reactor and then adding 200 mmol of Fmoc-Ile-OH and 400 mmol of diisopropylethylamine (DIEA), followed by dissolving well by stirring, the mixture was allowed to react for 1 hour while stirring. After the reaction, the mixture was washed and reacted for 10 minutes with methanol and DIEA (2:1) in DCM and then washed with excess DCM/DMF (1:1). After removing the solution and adding 10 mL of dimethylformamide (DMF), the mixture was stirred for 3 minutes and then the solvent was removed. After adding 10 mL of a deprotecting solution (20% piperidine/DMF) to the reactor, the mixture was stirred at room temperature for 10 minutes and the solution was removed. After adding the same volume of the deprotecting solution and performing reaction for 10 minutes, the solution was removed and Ile-CTL resin was obtained by washing twice with DMF, once with MC and then 3 times again with DMF, for 3 minutes each. To a new reactor, 10 mL of DMF was added. Then, 200 mmol of Fmoc-Tyr(tBu)-OH, 200 mmol of HoBt and 200 mmol of Bop were added and dissolved by stirring. After adding 400 mmol of DIEA to the reactor with two fractions, the mixture was stirred for at least 5 minutes until all solid was dissolved. The resulting amino acid mixture solution was added to the reactor holding the deprotected resin and reacted by stirring at room temperature for 1 hour. After removing the reaction solution and stirring 3 times with DMF, for 5 minutes each, the DMF was removed. A small amount of the reacted resin was taken and the degree of reaction was examined by the Kaiser test (ninhydrin test). The resin was deprotected twice using the deprotecting solution in the same manner described above to obtain Tyr(tBu)-Ile-CTL resin. After washing sufficiently with DMF and MC, the Kaiser test was carried out once again and amino acids were attached as described above. Then, Fmoc-KWTLALKSDY-ISLLASGTYLATAYI-CTL (SEQ ID NO: 22) resin was prepared by polymerase chain reaction based on the determined amino acid sequence, as shown in FIG. 1. The resulting peptide has all its residues protected. The prepared peptidyl resin was 3 times with DMF, MC and methanol, respectively, and dried by slowly flowing nitrogen. After completely vacuum-drying under $P_2O_5$ atmosphere, the resin was added to 30 mL of 0.1% trifluoroacetic acid and kept at room temperature for 2 hours with shaking. The resin was filtered and washed with a small volume of 0.1% TFA solution, after which the filtrate was combined with the mother liquor. After neutralization with pyridine and distillation under reduced pressure to reduce the total volume to half, precipitation was induced by adding 50 mL of cold ether. After centrifugation, the precipitate was recovered and washed twice with cold ether. After removing the mother liquor, the resultant was sufficiently dried under nitrogen atmosphere to yield 1.18 g of the product (yield: 47.6%).

(2) Production of Water-Soluble Resin (2 Residues)

After accurately measuring the spacing of the base region of membrane proteins available, for example, from PDB Data, a linker having 1-10 aminohexanoic acid or glycine residues was prepared for synthesis of a loop-type peptide. For attachment with resin, L-Lys (Mtt) was located at the middle residue (e.g., Fmoc-Gly-Gly-Glu(OAII)-Gly-Gly-COOH (SEQ ID NO: 23), Fmoc-AHX-AHX-Lys(Mtt)-AHX-AHX-COOH) (SEQ ID NO: 24). After attaching to NOVAGEL™-HMBA resin (Novagen), the amino group at the N-terminal was deprotected. The water-soluble resin of the present disclosure, which is modified with polyethylene glycol (PEG), is mass producible and can be prepared with different sizes.

(3) Production of Loop-Type Peptidyl Resin

The peptide of SEQ ID NO: 1 prepared in 1), whose all residues are protected, was coupled with the water-soluble resin prepared in 2). After reaction in the presence of HoBt and HBTU with adequately controlled DIEA, the completion of the reaction was confirmed by ninhydrin test. After removing all unreacted substances, the allyl group was removed in the presence of $Pd(Ph_3P)_4/CHCl_3/AcOH/NMN$ and the Fmoc (fluorenylmethyloxycarbonyl) at the N-terminal was deprotected. After reaction in the presence of HoBt and HBTU with adequately controlled DIEA again, the completion of the reaction was confirmed by ninhydrin test. The following loop-type peptide was synthesized.

```
                                           (SEQ ID NO: 1)
KWTLALKSDYISLLASGTYLATAYIE-linker-resin (1-26 cyclized)
```

Figure 3A:
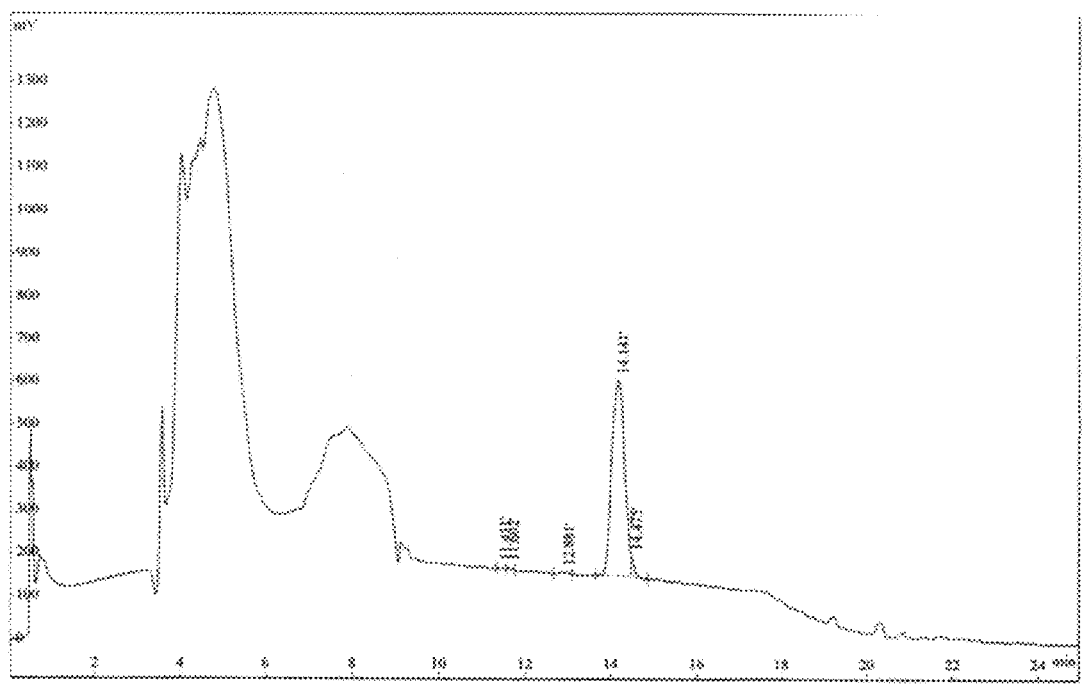
FIGS. 3A and 3B show HPLC and mass analysis results of a synthesized peptide of SEQ ID NO: 1, respectively.
Figure 3B:
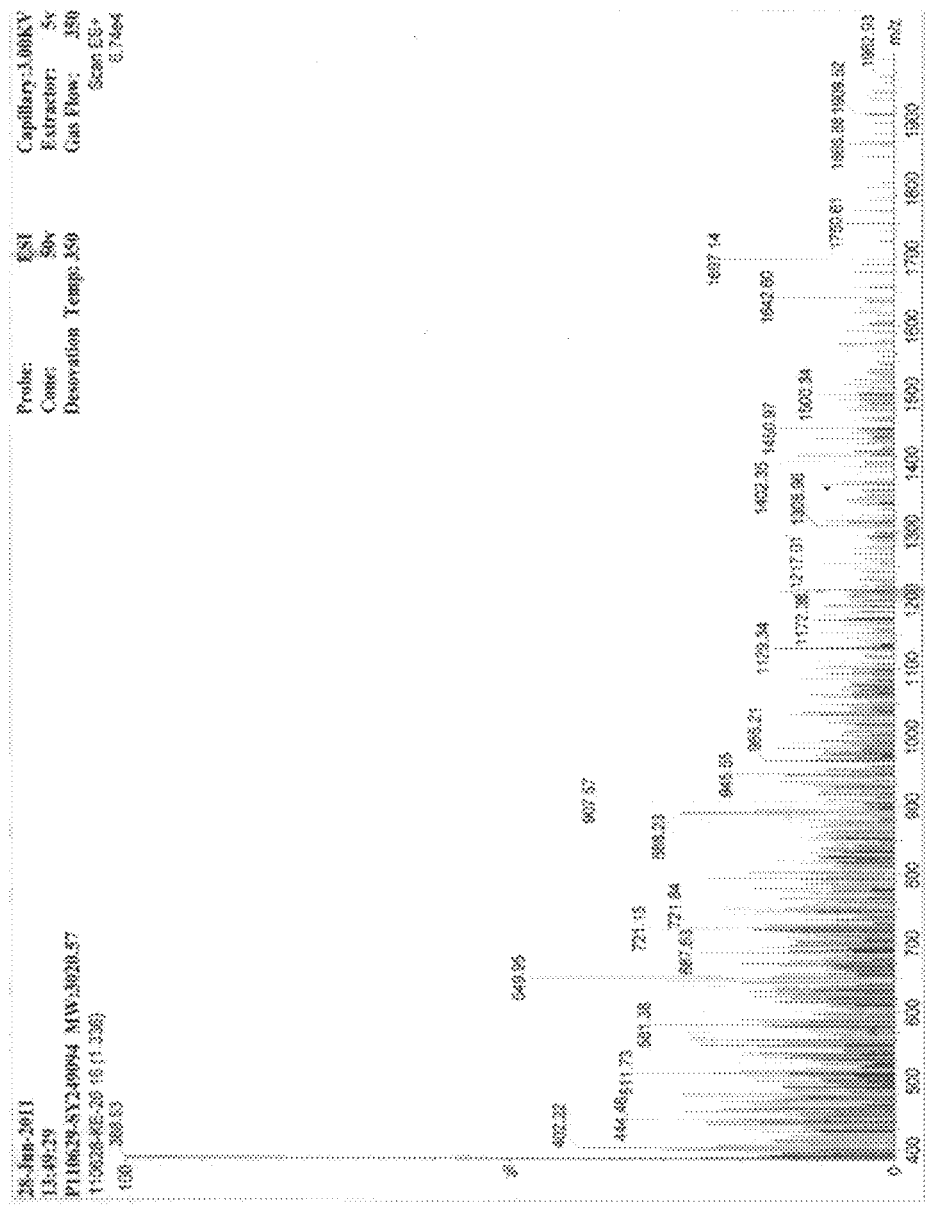

HPLC and mass analyses revealed that the desired peptide was synthesized, as shown in FIGS. 3A and 3B. Sequence data of the synthesized loop-type peptides are given in Table 1.

TABLE 1

Sequence data of synthesized loop-type peptides

| SEQ ID NO | Protein name | Sequence | Note |
|---|---|---|---|
| 1 | CD-151-1 | KWTLALKSDYISLLASGTYLATAYIE-Linker-Resin ((SEQ ID NO: 1)-Linker Resin) | Peptide |
| 2 | CD151-2 | C-GSNNSQDWR DSEWIRSQEA GGRVVPDSCC KTVVALCGQR DHASNIYKVE GG-C (C-(SEQ ID NO: 2-C) | Protein |
| 3 | Claudin 3 | SANTIIRDFYNPVVPEAQKREMGA(SEQ ID NO: 3)GE-Linker-Resin((SEQ ID NO: 3)GE-Linker-Resin) C-SANTIIRDFYNPVVPEAQKREMGAGE-C (C-(SEQ ID NO: 3)-C) | Peptide/ protein |
| 4 | Claudin 4 | TAHNIIQDFYNPLASGQKREMGASE-Linker-Resin ((SEQ ID NO: 4)E-Linker-Resin) C-TAHNIIQDFYNPLASGQKREMGASE-C (C-(SEQ ID NO: 4)E-C) | Peptide/ protein |
| 5 | Claudin 5 | FANIVVREFYDPSVPVSQKYELGAAE-Linker-Resin ((SEQ ID NO: 5)-Linker-Resin) | Peptide |
| 6 | Claudin 6 | TAHAVIRDFYNPLVAEAQKRELGASE-Linker-Resin ((SEQ ID NO: 6)-Linker-Resin) | Peptide |
| 7 | Claudin 7 | VANAIIRDFYNSIVNVAQKRELGEAE-Linker-Resin ((SEQ ID NO: 7)-Linker-Resin) | Peptide |

TABLE 1-continued

Sequence data of synthesized loop-type peptides

| SEQ ID NO | Protein name | Sequence | Note |
|---|---|---|---|
| 8 | Claudin 9 | TAHAIIQDFYNPLVAEALKRELGASE-Linker-Resin ((SEQ ID NO: 8)-Linker-Resin) | Peptide |
| 9 | Claudin 17 | TANIIIRDFYNPAIHIGQKRELGAAE-Linker-Resin ((SEQ ID NO: 9)-Linker-Resin) | Peptide |
| 10 | CPE protein | KLVMKANSSYSGNYPYSILFQKE-Linker-Resin ((SEQ ID NO: 10)-Linker-Resin) | Peptide |
| 11 | CPE protein | KANSSYSGNYPYSILFQKE-Linker-Resin ((SEQ ID NO: 11)-Linker-Resin) | Peptide |
| 12 | CD151-3 | KGSNNSQDWRDSEWIRSQEAGGRVVPDSE-Linker-Resin ((SEQ ID NO: 12)-Linker-Resin) | Peptide |
| 13 | CD151-4 | KKTVVALCGQRDHASNIYKVEGGE-Linker-Resin ((SEQ ID NO: 13)-Linker-Resin) | Peptide |
| 14 | CD151-5 | WTLALJSDYUSLLASGTYLATAYIE-Linker-Resin ((SEQ ID NO: 14)-Linker-Resin) | Peptide |
| 15 | CD151 -6 | C-AYYQQLNTELKENLKDTMTKRYHQPGHEAVTSAVDQLQQE FH-C ((SEQ ID NO: 15)-Linker-Resin) | Peptide |
| 16 | CD9-1 | KRFDSQTKSIFEQETNNNNSSFYTGVE-Linker-Resin ((SEQ ID NO: 16)-Linker-Resin) | Peptide |
| 17 | CD9-2 | KDEVIKEVQEFYKDTYNKLKTKDEPQRETLE-Linker-Resin ((SEQ ID NO: 17)-Linker-Resin) | Peptide |
| 18 | CD9-3 | C-GLAGGVEQFISDIC(S)PKKDVLETFTVKS-C (C-(SEQ ID NO: 18)-C) | Protein |
| 19 | UP1b-1 | KFVSDQHSLYPLLEATDNDDIYGAAWIGIFVE-Linker-Resin ((SEQ ID NO: 19)-Linker-Resin) | Peptide |
| 20 | UP 1b-2 | KQMLERYQNNSPPNNDDQWKNNGVTKE-Linker-Resin ((SEQ ID NO: 20)-Linker-Resin) | Peptide |
| 21 | UP1b-3 | C-GVNGPSDWQKYTSFRTENNDADYPWPRQC(S)C(S)VMNNL KEPLNLEAC(S)KLGVPGFYHNQGC-C (C (SEQ ID NO: 17)-C) | Protein |

Example 2: Synthesis of Loop-Type Protein

Figure 4:
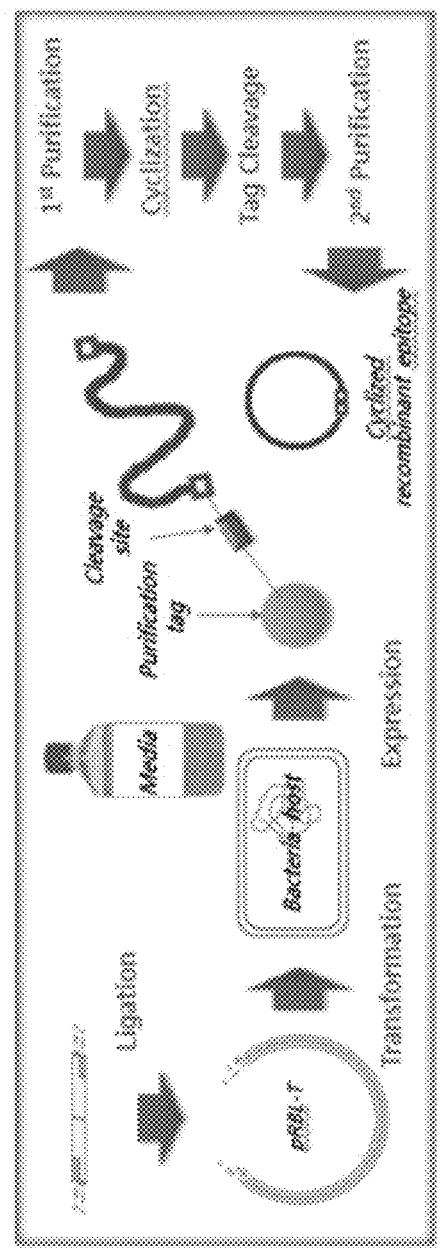
FIG. 4 schematically describes production of a loop-type protein.

In order to produce the loop-type protein shown in FIG. 4, cloning was performed using the claudin proteins of SEQ ID NOS: 3 and 4 described in Table 1.

Reverse transcription PCR(RT-PCR) or primer overlap extension PCR (overlap extension PCR) was conducted for tcggccaacaccattatccgggacttctacaaccccgtggtgcccg aggcgcagaagcgcgagatgggcgcgggc (SEQ ID NO: 25) which is a DNA base sequence for the extracellular loop sequence of claudin 3, SANTIIRDFYNPVVPEAQKREMGA (SEQ ID NO: 3), or for acggcccacaacatcatccaagacttctacaatccgctggtggcctc-cgggcagaagegggagatgggtgcctcg (SEQ ID NO: 26) which is a DNA base sequence for the extracellular loop sequence of claudin 4, TAHNIIQDFYNPLASGQKREMGAS (SEQ ID NO: 4). For preparation of a cyclized recombinant peptide, TGT or TGC coding for the cysteine residue was inserted at the end. For connection with a vector, CATATG and CTCGAG, which are sites to be cleaved by the restriction enzymes NdeI and XhoI, respectively, were inserted in 5' and 3' directions. A stop codon (TAA) was inserted in front of the XhoI cleavage site. Finally, CATATG-TGT(C)-tcggc-caacaccattatccgggacttctacaaccccgtggtgcccgaggcgcaga agcgcgagatgggcgcgggc(SEQ ID NO: 25)-TGT(C)-TAA-CTCGAG and CATATG-TGT(C)-acggcccacaacatc atc-caagacttctacaatccgctggtggcctccgggcagaagcgggagatgggtgc-ctcg (SEQ ID NO: 26)-TGT(C)-TAA-CTCGAG genes were obtained for claudin 3 and claudin 4, respectively. A pREP-HTX vector, a T7 promoter and an ampicillin-resistant selective marker were used. The construct has a hexahistidine tag and a thrombin cleavage site.

Thus obtained vector and claudin peptide gene were cleaved by treating with the restriction enzymes NdeI and XhoI, respectively. After determining size on agarose gel, the vector and the peptide gene were purified and then ligated. The vector and the peptide gene were using T4 ligase at a ratio of vector:gene=1:3.

The ligation was conducted at 15° C. for 4 hours. After the ligation was completed, the resultant was transformed with competent cell DH5α. After the transformation was completed, the cells were grown on Luria-Bertani (LB) agar containing 50 μg/mL ampicillin at 37° C. for 18 hours. Among thus obtained colonies, those containing the target gene were selected by PCR test.

After incubation on liquid LB containing ampicillin at 37° C. and 180 rpm, 1 mM isopropyl β-D-1-thiogalactopyranoside (IPTG) was added when the absorbance at 600 nm reached about 0.7 and expression was carried out at 30° C. for 4 or more hours. After the expression was completed, only the expressed cells were recovered by centrifuging the whole culture medium (4° C., 5,000 rpm, 15 minutes). The expressed cells were lysed under high pressure. The expressed cells were lysed after suspending in nickel affinity chromatography buffer containing pH 8.0 Tris buffer, 5 mM imidazole and 0.5 M sodium chloride. The cell lysate was centrifuged with a high-speed centrifuge at 10,000 rpm or above and only the supernatant was taken. After nickel affinity chromatography, the cysteine residue at the end of the protein was reduced with 10 mM dithiothreitol (DTT) using a column coupled to the chromatography system. Then, on-column refolding was conducted by replacing with the nickel affinity chromatography buffer described above. Then, the protein was cleaved using a thrombin cleavage solution. The restriction was carried out at room temperature by maintaining in the thrombin cleavage solution for at least 12 hours. After the restriction was completed with 1 unit per mg of the protein, only the cleaved protein antigen was recovered by flowing nickel affinity chromatography buffer.

Figure 5:
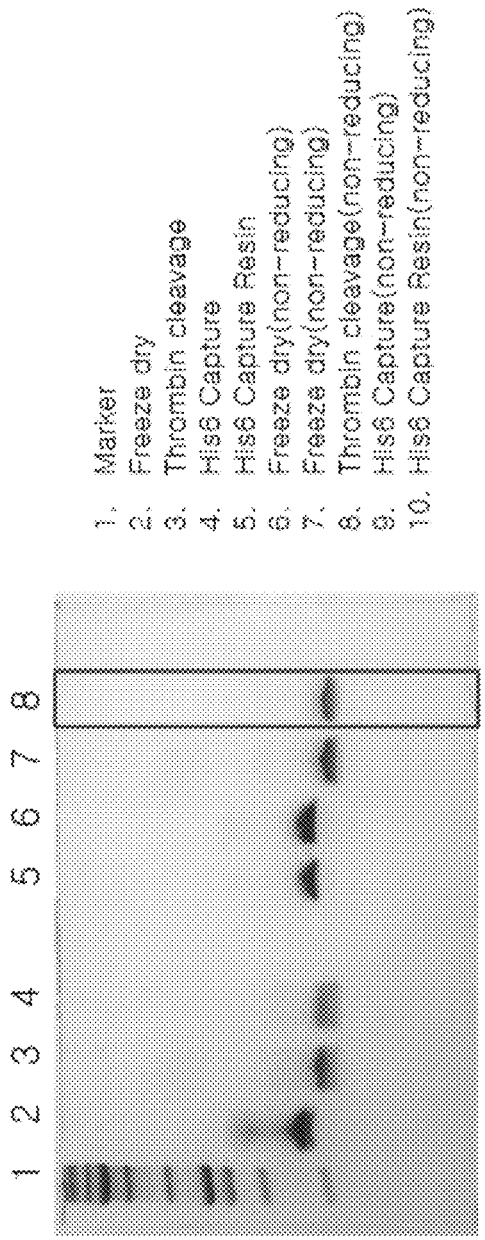
FIG. 5 shows an SDS-PAGE result of an expressed loop-type peptide of SEQ ID NO: 2.

Thus purified protein antigen was subjected to SDS-PAGE gel electrophoresis under non-denaturing condition. Then, only the monomers were isolated by gel filtration to obtain the finally purified cyclized protein antigen. FIG. 5 shows the SDS-PAGE for CD151-2 of SEQ ID NO: 2.

Example 3: Library Screening Using Loop-Type Peptide and Protein

Figure 6:
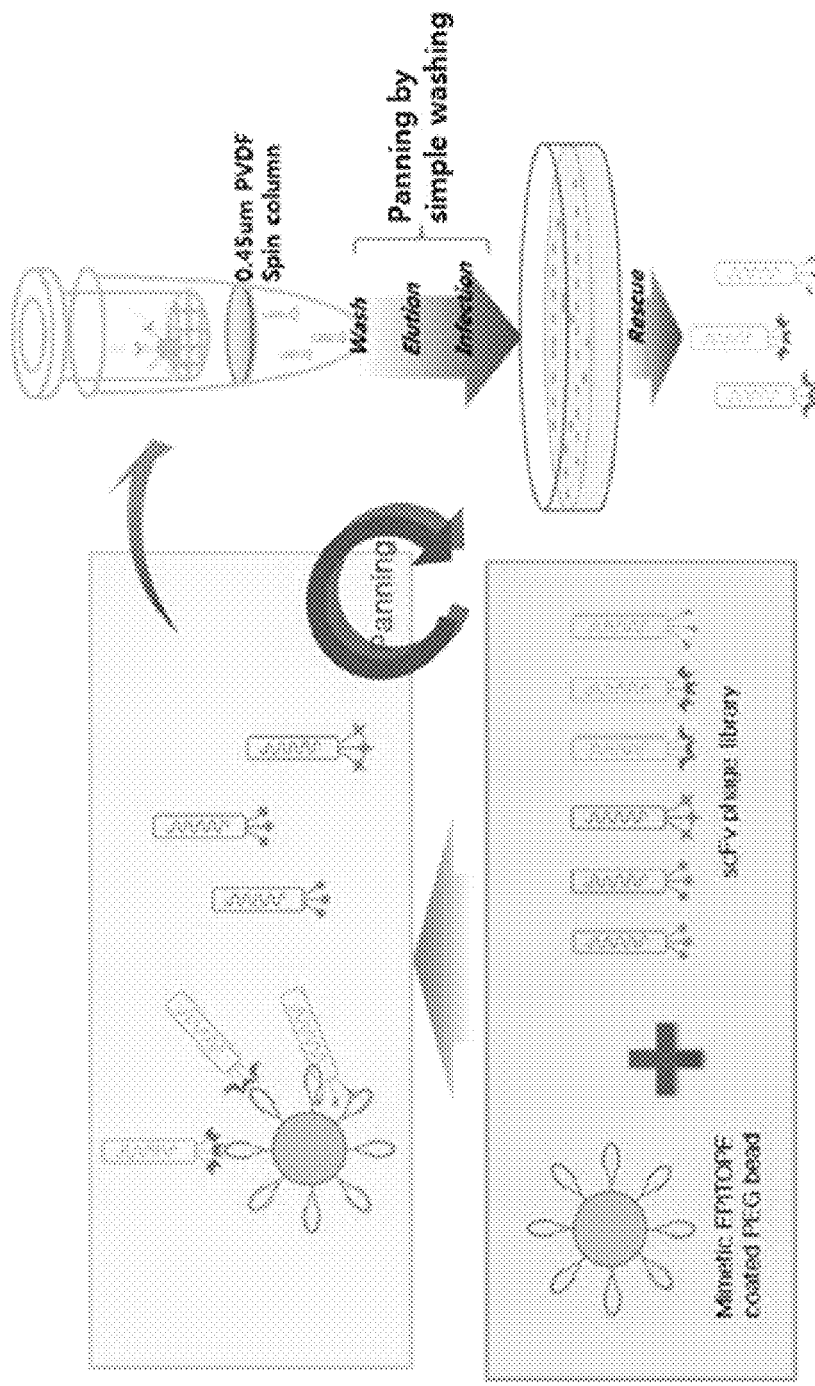
FIG. 6 schematically describes library screening using the prepared loop-type antigen.
Figure 7:
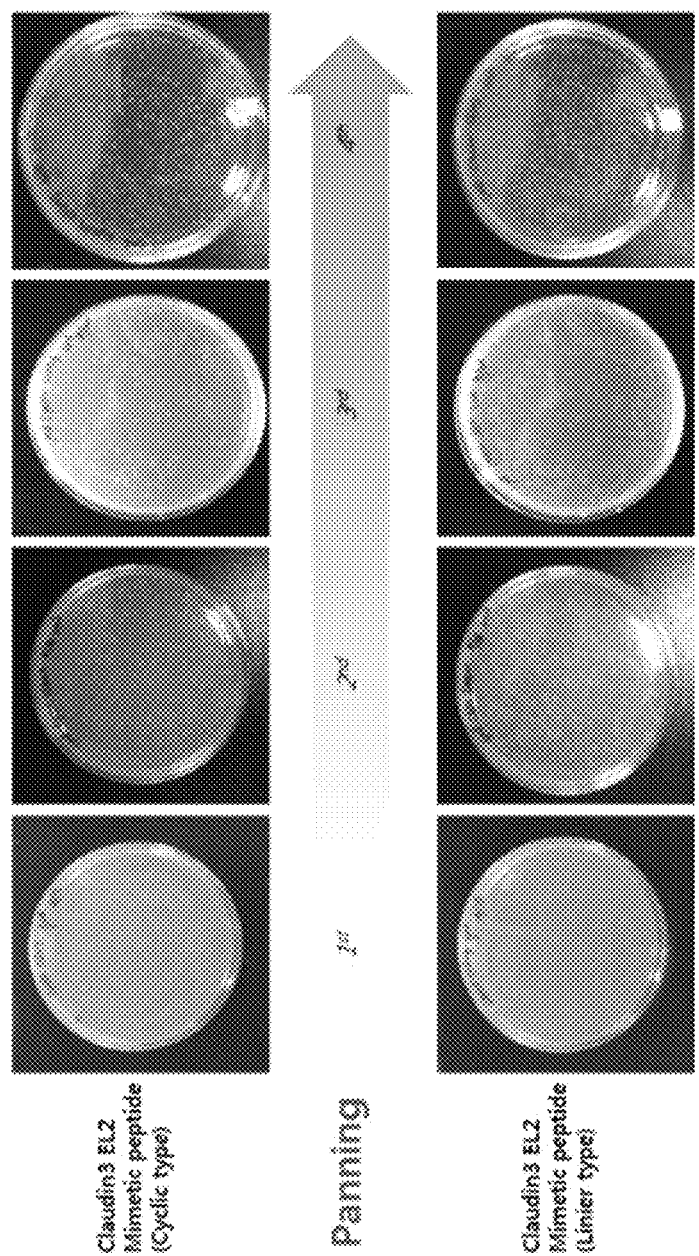
FIG. 7 shows a result of screening and panning an antigen of a multi-transmembrane protein.

The loop-type peptide resin of claudin-3 of SEQ ID NO: 3 prepared in Example 1 and a linear peptide resin were compared by the phage library display for screening of the claudin protein and antibodies binding specifically to the claudin protein and comparison of stereostructure. As schematically described in FIG. 6, *E. coli* TG1 cells were inoculated to LB medium and cultured until the mid-log phase. After reacting claudin peptide bound to beads with a humanized antibody library solution at room temperature for 1 hour, only the beads were recovered. After washing 3 times with TBS-T, the beads were transferred to a membrane filter tube and reacted for 10 minutes in 100 mM triethylamine (TEA) at room temperature in order to separate the humanized antibody library bound to the bead-claudin peptide. The separated humanized antibody library solution was neutralized with Tris-HCl (pH 7.4) and inoculated to the *E. coli* TG1 cells cultured above. After incubation at 37° C. for 1 hour, the culture was further incubated at 37° C. for 16 hours in an agar medium containing ampicillin and 2% glucose. After adding 5 mL of LB medium to the agar medium and spreading the colony with a spreader, 50 µL was inoculated to LB medium containing ampicillin and cultured at 37° C. After reaching the mid-log phase, 500 µl, of $1\times10^{11}$/mL VCSM13 helper phage was inoculated. After incubation for 1 hour, 70 ng/mL kanamycin was inoculated. After incubation at 37° C. for 16 hours, the culture was centrifuged and the supernatant was recovered and reacted for 30 minutes in a refrigerator by adding 20% PEG8000 containing 15% NaCl. After centrifugation, the supernatant was removed and the remaining pellet was suspended well in 500 µL of PBS and centrifuged at 12,000 rpm for 10 minutes. Then, the supernatant was recovered. This procedure was repeated 3 more times. FIG. 6 schematically illustrates library screening using the prepared loop-type antigen and FIG. 7 shows a result of panning the antigen of the claudin protein. In order to measure the titer of the panned library candidates, ELISA was carried out as follows. 100 µL of biotinylated claudin peptide was attached to a microtiter plate at 10 mg/mL concentration per well and, after sufficient washing, non-specific binding was prevented using 5% skim milk. After washing with TBS-Tween 20, antibody fragments expressed by *E. coli* were attached for 1 hour. After sufficiently washing the plate, the antibody fragments fixed to the plate were bound at room temperature for 1 hour by adding anti-HA-horseradish peroxidase. After sufficient washing, a peroxidase substrate solution (TMB) was added and absorbance was measured at 450 nm. Through this, candidate antibody fragments were screened primarily. As seen from FIG. 8, the screening result shows that antibody fragments with high reactivity are screened better in the 3-dimensional antigen than the linear antigen. In addition, the inventors of the present disclosure further synthesized scFv and screened antibody fragments or antibodies using the traditional hybridoma screening method.

Example 4: FACS Analysis of Selected scFv

Figure 9:
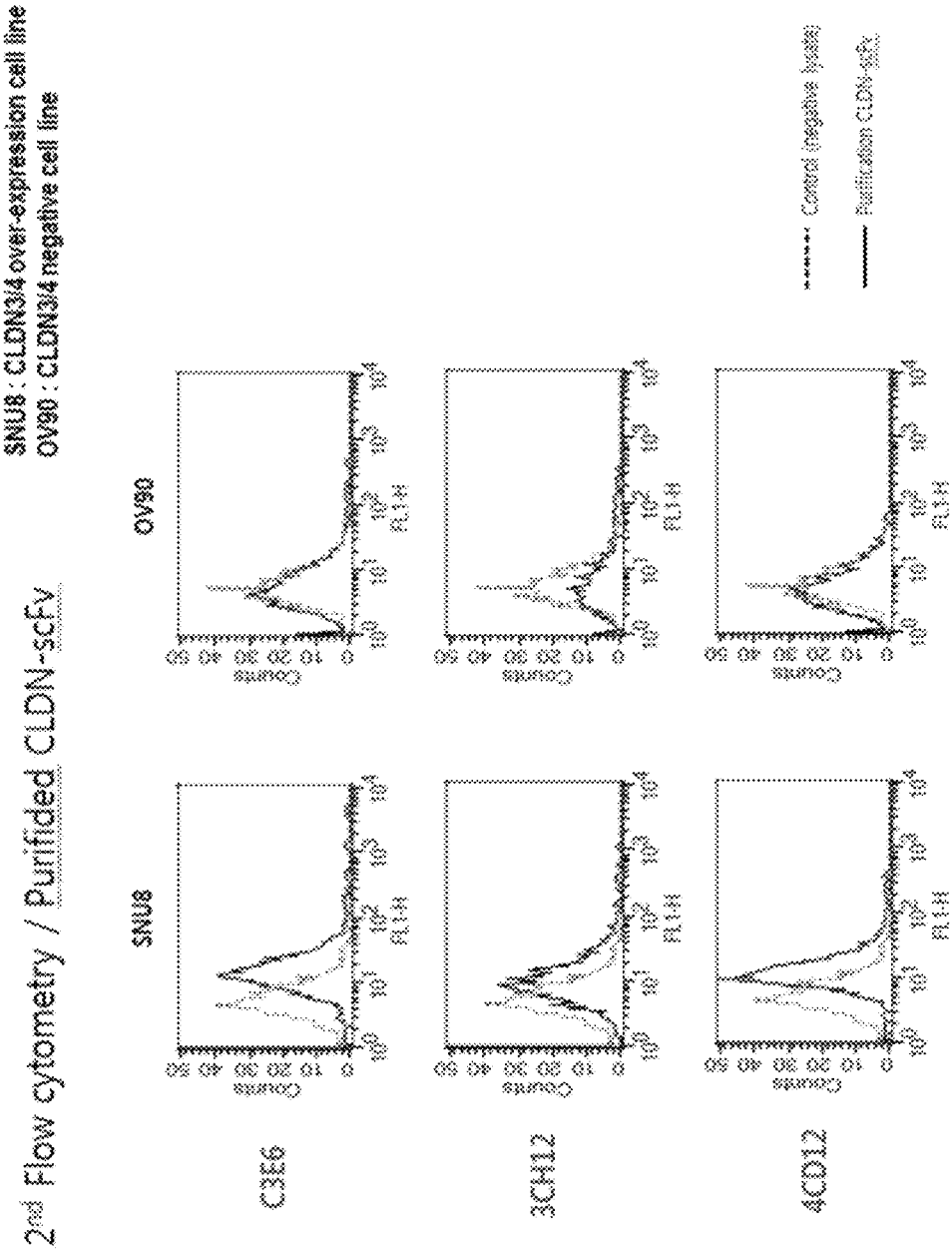
FIG. 9 shows a result of analyzing the efficiency of selected loop-type and linear antibodies by FACS.

The antibody fragments primarily screened from the linear and loop-type antigens were sub-cloned to *E. coli*. After expression and purification, FACS analysis was performed to investigate the usefulness of the 3-dimensional loop-type antigen. For FACS analysis, SNU-8 stomach cancer cells (Korean Cell Line Bank, Korea) in which claudin is overexpressed were used as target cells. Cell density was adjusted to $2\times10^6$/mL per 1 mL sample. After culturing the cells in RPMI 1640 medium (Hyclone) containing 10% FBS, the cells were harvested and washed with PBS. After attaching the prepared antibodies for 1 hour, the cells were washed once again with PBS. After attaching HA-FITC Ig for 1 hour, binding was evaluated using the FacsCalibur™ flow cytometer (Becton Dickinson). The same procedure was carried out for OV-90 cells as control. As seen from FIG. 9, the expressed loop-type antigen showed the best efficiency.

Example 5: SPR Analysis of Selected scFv

For measurement of the specificity of the antibody fragment prepared in the present disclosure for anti-claudin, claudin peptide was attached onto the PROTEON™ GLC sensor chip and surface plasmon resonance (SPR) binding assay was carried out using the antibody fragments screened and purified from the prepared linear and loop-type peptides. The test procedure followed the instructions of Bio-Rad. As seen from FIG. 10, the loop-type antigen scFv exhibited about 1,000 times higher binding ability than the linear antigen scFv.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A multi-transmembrane protein antigen comprising a polypeptide corresponding to an extracellular loop of a multi-transmembrane protein, wherein an N-terminal and a C-terminal of the polypeptide are fixed on a solid substrate, or an N-terminal and a C-terminal of the polypeptide are attached to both ends of a linker to form a cyclic structure, wherein polypeptide corresponding to the extracellular loop of the multi-transmembrane protein is a polypeptide consisting of the amino acid sequence of SEQ ID NO: 3 or 4.

2. The antigen according to claim 1, wherein the N-terminal and the C-terminal of the polypeptide are fixed on the solid substrate.

3. The antigen according to claim 1, wherein the N-terminal and the C-terminal of the polypeptide are attached to both ends of the linker to form the cyclic structure.

4. The antigen according to claim 3, wherein the linker is selected from the group consisting of aminohexanoic acid, polyglycine and polyalanine.

5. The antigen according to claim 3, wherein the linker is attached to a water-soluble resin.

6. The antigen according to claim 5, wherein the water-soluble resin is enclosed by polyethylene glycol (PEG).

* * * * *

SEQUENCE LISTING

<160> NUMBER OF SEQ ID NOS: 26

<210> SEQ ID NO 1
<211> LENGTH: 26
<212> TYPE: PRT
<213> ORGANISM: Homo sapiens

<400> SEQUENCE: 1

Lys Trp Thr Leu Ala Leu Lys Ser Asp Tyr Ile Ser Leu Leu Ala Ser
1               5                   10                  15

Gly Thr Tyr Leu Ala Thr Ala Tyr Ile Glu
            20                  25

<210> SEQ ID NO 2
<211> LENGTH: 51
<212> TYPE: PRT
<213> ORGANISM: Homo sapiens

<400> SEQUENCE: 2

Gly Ser Asn Asn Ser Gln Asp Trp Arg Asp Ser Glu Trp Ile Arg Ser
1               5                   10                  15

Gln Glu Ala Gly Gly Arg Val Val Pro Asp Ser Cys Cys Lys Thr Val
            20                  25                  30

Val Ala Leu Cys Gly Gln Arg Asp His Ala Ser Asn Ile Tyr Lys Val
        35                  40                  45

Glu Gly Gly
    50

<210> SEQ ID NO 3
<211> LENGTH: 24
<212> TYPE: PRT
<213> ORGANISM: Homo sapiens

<400> SEQUENCE: 3

Ser Ala Asn Thr Ile Ile Arg Asp Phe Tyr Asn Pro Val Val Pro Glu
1               5                   10                  15

Ala Gln Lys Arg Glu Met Gly Ala
            20

<210> SEQ ID NO 4
<211> LENGTH: 24
<212> TYPE: PRT
<213> ORGANISM: Homo sapiens

<400> SEQUENCE: 4

Thr Ala His Asn Ile Ile Gln Asp Phe Tyr Asn Pro Leu Ala Ser Gly
1               5                   10                  15

Gln Lys Arg Glu Met Gly Ala Ser
            20

<210> SEQ ID NO 5
<211> LENGTH: 26
<212> TYPE: PRT
<213> ORGANISM: Homo sapiens

<400> SEQUENCE: 5

Phe Ala Asn Ile Val Val Arg Glu Phe Tyr Asp Pro Ser Val Pro Val
1               5                   10                  15

Ser Gln Lys Tyr Glu Leu Gly Ala Ala Glu
            20                  25

```
<210> SEQ ID NO 6
<211> LENGTH: 26
<212> TYPE: PRT
<213> ORGANISM: Homo sapiens

<400> SEQUENCE: 6

Thr Ala His Ala Val Ile Arg Asp Phe Tyr Asn Pro Leu Val Ala Glu
 1               5                  10                  15

Ala Gln Lys Arg Glu Leu Gly Ala Ser Glu
            20                  25

<210> SEQ ID NO 7
<211> LENGTH: 26
<212> TYPE: PRT
<213> ORGANISM: Homo sapiens

<400> SEQUENCE: 7

Val Ala Asn Ala Ile Ile Arg Asp Phe Tyr Asn Ser Ile Val Asn Val
 1               5                  10                  15

Ala Gln Lys Arg Glu Leu Gly Glu Ala Glu
            20                  25

<210> SEQ ID NO 8
<211> LENGTH: 26
<212> TYPE: PRT
<213> ORGANISM: Homo sapiens

<400> SEQUENCE: 8

Thr Ala His Ala Ile Ile Gln Asp Phe Tyr Asn Pro Leu Val Ala Glu
 1               5                  10                  15

Ala Leu Lys Arg Glu Leu Gly Ala Ser Glu
            20                  25

<210> SEQ ID NO 9
<211> LENGTH: 26
<212> TYPE: PRT
<213> ORGANISM: Homo sapiens

<400> SEQUENCE: 9

Thr Ala Asn Ile Ile Ile Arg Asp Phe Tyr Asn Pro Ala Ile His Ile
 1               5                  10                  15

Gly Gln Lys Arg Glu Leu Gly Ala Ala Glu
            20                  25

<210> SEQ ID NO 10
<211> LENGTH: 23
<212> TYPE: PRT
<213> ORGANISM: Homo sapiens

<400> SEQUENCE: 10

Lys Leu Val Met Lys Ala Asn Ser Ser Tyr Ser Gly Asn Tyr Pro Tyr
 1               5                  10                  15

Ser Ile Leu Phe Gln Lys Glu
            20

<210> SEQ ID NO 11
<211> LENGTH: 19
<212> TYPE: PRT
<213> ORGANISM: Homo sapiens

<400> SEQUENCE: 11

Lys Ala Asn Ser Ser Tyr Ser Gly Asn Tyr Pro Tyr Ser Ile Leu Phe
 1               5                  10                  15
```

Gln Lys Glu

<210> SEQ ID NO 12
<211> LENGTH: 29
<212> TYPE: PRT
<213> ORGANISM: Homo sapiens

<400> SEQUENCE: 12

Lys Gly Ser Asn Asn Ser Gln Asp Trp Arg Asp Ser Glu Trp Ile Arg
1               5                   10                  15

Ser Gln Glu Ala Gly Gly Arg Val Val Pro Asp Ser Glu
            20                  25

<210> SEQ ID NO 13
<211> LENGTH: 24
<212> TYPE: PRT
<213> ORGANISM: Homo sapiens

<400> SEQUENCE: 13

Lys Lys Thr Val Val Ala Leu Cys Gly Gln Arg Asp His Ala Ser Asn
1               5                   10                  15

Ile Tyr Lys Val Glu Gly Gly Glu
            20

<210> SEQ ID NO 14
<211> LENGTH: 25
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is leucine or isoleucine
<220> FEATURE:
<221> NAME/KEY: MISC_FEATURE
<222> LOCATION: (10)..(10)
<223> OTHER INFORMATION: Xaa is selenocysteine

<400> SEQUENCE: 14

Trp Thr Leu Ala Leu Xaa Ser Asp Tyr Xaa Ser Leu Leu Ala Ser Gly
1               5                   10                  15

Thr Tyr Leu Ala Thr Ala Tyr Ile Glu
            20                  25

<210> SEQ ID NO 15
<211> LENGTH: 40
<212> TYPE: PRT
<213> ORGANISM: Homo sapiens

<400> SEQUENCE: 15

Ala Tyr Tyr Gln Gln Leu Asn Thr Glu Leu Lys Glu Asn Leu Lys Asp
1               5                   10                  15

Thr Met Thr Lys Arg Tyr His Gln Pro Gly His Glu Ala Val Thr Ser
            20                  25                  30

Ala Val Asp Gln Leu Gln Gln Glu
            35                  40

<210> SEQ ID NO 16
<211> LENGTH: 27
<212> TYPE: PRT
<213> ORGANISM: Homo sapiens

<400> SEQUENCE: 16

Lys Arg Phe Asp Ser Gln Thr Lys Ser Ile Phe Glu Gln Glu Thr Asn

```
                1               5                       10                      15
Asn Asn Asn Ser Ser Phe Tyr Thr Gly Val Glu
                        20                      25

<210> SEQ ID NO 17
<211> LENGTH: 31
<212> TYPE: PRT
<213> ORGANISM: Homo sapiens

<400> SEQUENCE: 17

Lys Asp Glu Val Ile Lys Glu Val Gln Glu Phe Tyr Lys Asp Thr Tyr
1               5                   10                  15

Asn Lys Leu Lys Thr Lys Asp Glu Pro Gln Arg Glu Thr Leu Glu
            20                  25                  30

<210> SEQ ID NO 18
<211> LENGTH: 27
<212> TYPE: PRT
<213> ORGANISM: Homo sapiens
<220> FEATURE:
<221> NAME/KEY: MISC_FEATURE
<222> LOCATION: (14)..(14)
<223> OTHER INFORMATION: Xaa is cysteine or serine.

<400> SEQUENCE: 18

Gly Leu Ala Gly Gly Val Glu Gln Phe Ile Ser Asp Ile Xaa Pro Lys
1               5                   10                  15

Lys Asp Val Leu Glu Thr Phe Thr Val Lys Ser
            20                  25

<210> SEQ ID NO 19
<211> LENGTH: 32
<212> TYPE: PRT
<213> ORGANISM: Homo sapiens

<400> SEQUENCE: 19

Lys Phe Val Ser Asp Gln His Ser Leu Tyr Pro Leu Leu Glu Ala Thr
1               5                   10                  15

Asp Asn Asp Asp Ile Tyr Gly Ala Ala Trp Ile Gly Ile Phe Val Glu
            20                  25                  30

<210> SEQ ID NO 20
<211> LENGTH: 27
<212> TYPE: PRT
<213> ORGANISM: Homo sapiens

<400> SEQUENCE: 20

Lys Gln Met Leu Glu Arg Tyr Gln Asn Asn Ser Pro Pro Asn Asn Asp
1               5                   10                  15

Asp Gln Trp Lys Asn Asn Gly Val Thr Lys Glu
            20                  25

<210> SEQ ID NO 21
<211> LENGTH: 57
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Xaa is Cysteine or Serine.
<220> FEATURE:
<221> NAME/KEY: MISC_FEATURE
<222> LOCATION: (30)..(30)
<223> OTHER INFORMATION: Xaa is Cysteine or Serine.
<220> FEATURE:
```

```
<221> NAME/KEY: MISC_FEATURE
<222> LOCATION: (44)..(44)
<223> OTHER INFORMATION: Xaa is Cysteine or Serine.

<400> SEQUENCE: 21

Gly Val Asn Gly Pro Ser Asp Trp Gln Lys Tyr Thr Ser Phe Arg Thr
1               5                   10                  15

Glu Asn Asn Asp Ala Asp Tyr Pro Trp Pro Arg Gln Xaa Xaa Val Met
                20                  25                  30

Asn Asn Leu Lys Glu Pro Leu Asn Leu Glu Ala Xaa Lys Leu Gly Val
            35                  40                  45

Pro Gly Phe Tyr His Asn Gln Gly Cys
    50                  55

<210> SEQ ID NO 22
<211> LENGTH: 25
<212> TYPE: PRT
<213> ORGANISM: Homo sapiens

<400> SEQUENCE: 22

Lys Trp Thr Leu Ala Leu Lys Ser Asp Tyr Ile Ser Leu Leu Ala Ser
1               5                   10                  15

Gly Thr Tyr Leu Ala Thr Ala Tyr Ile
            20                  25

<210> SEQ ID NO 23
<211> LENGTH: 5
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is Glu(OAll)

<400> SEQUENCE: 23

Gly Gly Xaa Gly Gly
1               5

<210> SEQ ID NO 24
<211> LENGTH: 13
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Lys(Mtt)
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid

<400> SEQUENCE: 24

Ala His Xaa Ala His Xaa Xaa Ala His Xaa Ala His Xaa
1               5                   10
```

```
<210> SEQ ID NO 25
<211> LENGTH: 75
<212> TYPE: DNA
<213> ORGANISM: Homo sapiens

<400> SEQUENCE: 25
tcggccaaca ccattatccg ggacttctac aacccgtgg tgcccgaggc gcagaagcgc      60
gagatgggcg cgggc                                                     75

<210> SEQ ID NO 26
<211> LENGTH: 75
<212> TYPE: DNA
<213> ORGANISM: Homo sapiens

<400> SEQUENCE: 26
acggcccaca acatcatcca agacttctac aatccgctgg tggcctccgg gcagaagcgg    60
gagatgggtg cctcg                                                     75
```